United States Patent [19]

Blatchley et al.

[11] Patent Number: 4,835,390
[45] Date of Patent: May 30, 1989

[54] APPARATUS AND METHOD FOR MEASURING BULK DENSITY USING POSITRON SCATTERING AND ANNIHILATION

[75] Inventors: Charles C. Blatchley, Nashua, N.H.; Piran Sioshansi, Bedford, Mass.; Robert H. Leyse, Saratoga; John R. Scheibel, Palo Alto, both of Calif.

[73] Assignee: Electric Power Research Institute, Inc., Palo Alto, Calif.

[21] Appl. No.: 110,520

[22] Filed: Oct. 19, 1987

[51] Int. Cl.$^4$ .................. G01N 23/12; G01N 23/10; G01N 23/08
[52] U.S. Cl. .................. 250/356.1; 250/358.1; 250/360.1
[58] Field of Search .......... 250/358.1, 359.1, 360.1, 250/356.1, 356.2, 363 R, 363 SA

[56] References Cited

U.S. PATENT DOCUMENTS

| | | | |
|---|---|---|---|
| 3,100,395 | 8/1963 | Morley | 73/192 |
| 4,044,259 | 8/1977 | Wyton et al. | 250/360.1 |
| 4,064,438 | 12/1977 | Alex et al. | 250/358.1 |
| 4,180,185 | 12/1979 | Yamamoto et al. | 250/356.1 |
| 4,362,939 | 12/1982 | Horiuchi et al. | 250/358.1 |
| 4,415,804 | 11/1983 | Sowerby | 378/53 |
| 4,463,263 | 7/1984 | Padawer | 250/363 R |
| 4,506,541 | 3/1985 | Cunningham | 73/32 R |
| 4,582,992 | 5/1986 | Atwell et al. | 250/360.1 |
| 4,603,257 | 7/1986 | Packer et al. | 250/359.1 |

FOREIGN PATENT DOCUMENTS 0152000 11/1981 Fed. Rep. of Germany ... 250/358.1

*Primary Examiner*—Janice A. Howell
*Assistant Examiner*—William F. Rauchholz
*Attorney, Agent, or Firm*—Flehr, Hohbach, Test, Albritton & Herbert

[57] ABSTRACT

A device for monitoring the bulk density and/or mass flow rate of a material within a vessel using positron scattering and annihilation radiometry techniques. The positron source is disposed on one side of the vessel having walls while an annihilation region preferably forming a portion of the vessel walls is disposed on the other side of the vessel. A gamma ray detector disposed externally of the vessel and collimated from the positron source detects the absorption of the positrons within the annihilation region. Monitoring the number of positrons absorbed within the annihilation region facilitates estimating bulk density and mass flow rates.

20 Claims, 1 Drawing Sheet

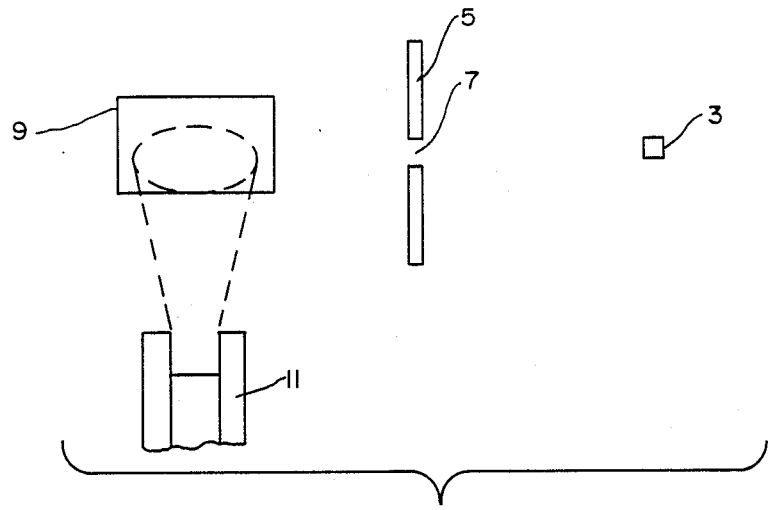
FIG.—1
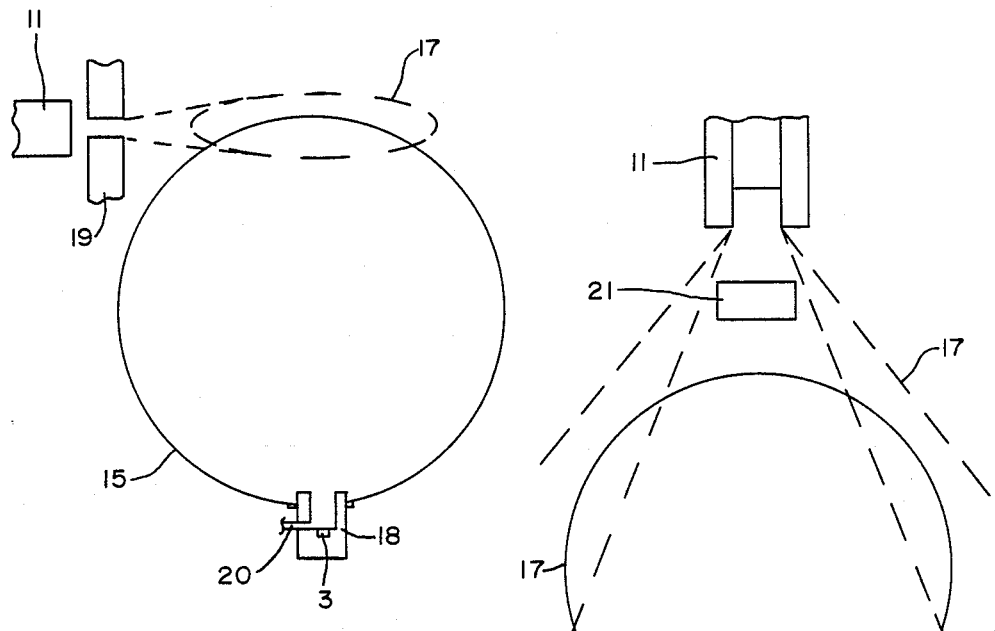
FIG.—2
FIG.—3

APPARATUS AND METHOD FOR MEASURING BULK DENSITY USING POSITRON SCATTERING AND ANNIHILATION

The present invention relates generally to radiometric measurements of a material's bulk density. More particularly, positrons are directed across a material such as a fluid stream and the effects of the material on the positrons is monitored for determining bulk density and, when appropriate, the mass flow rate.

A primary objective of this invention is to utilize the unique properties of positrons to precisely monitor the mass density of a flowing material. The invention was developed primarily to monitoring the combined mass density of pulverized coal in flow streams of air and/or other gases entrained with coal. Thus, the invention is described primarily with respect to that application. However, it will be appreciated that the invention may be applied to measure the bulk density of nonmoving materials and/or the mass flow rate of other flow streams as well.

Various radiometry techniques have been used to make density based fluid measurements. Such monitoring devices quantitatively determine the attenuation of radiation passing through a specific volume. Variations in attenuation of the radiation transmitted may be measured to nonintrusively indicate the changes in density or the amount of the material through which the radiation is passed. Gamma rays are the radiation form most commonly used in radiometry techniques. Indeed, gamma rays have successfully been employed in numerous applications such as fluid level monitoring. However, standard gamma ray radiometric approaches are not particularly well suited for sensing scale, sediment, ash deposits, or precipitates in piping since the density differences between the fluid passing through the piping and the precipitate itself are not always sharply defined. This is particularly true when dealing with contaminated fluids or when the fluid itself is a mixture which includes fine particles. Similarly, optical absorption meters are ineffective if a contaminant obscures light transmission or if the optical properties of the fluid mixture ar similar to those with a solid deposit.

Many industrial processes require the transportation of finely distributed particles within a fluid stream. However, it is often very difficult to accurately monitor the mass flow rates of such particulant/fluid streams. Taking, by way of example, the transportation of aerated pulverized coal, which is often used to fuel power plants, there are numerous variables which make accurate measuring difficult. To begin with, such particulant/fluid flow tends to be highly non-uniform with both unpredictable density concentrations and local vortices. Therefore, there is a need for a mass flow monitoring device that is capable of averaging the effects of these local non-uniformities.

Further, the pulverized coal is typically transported through large diameter pipes entrained in an air/coal fluid stream at relatively low pressures. Thus, it is necessary to monitor low density fluid flow over a wide flow path. It is noted that low density fluid streams are difficult to measure using beta (minus) particles, X-ray, or gamma ray radiometry. This is because a beam with an energy low enough to respond sensitively to the coal will typically not be able to penetrate the walls of the pipe through which it flows. Thus, both the source and the detector systems must be either directly exposed to the potentially highly corrosive flow or protected within windowed chambers. The attenuation of the signal caused by even thin windows requires fairly intense sources which can create a radiation hazard, particularly in the event of a fire or an explosion in the fluid line.

There is also a need to monitor the transportation and/or pumping of two-phase mixtures, slurries, or solutions which can produce precipitates or scale. In many cases, the solid deposits which result from transporting such mixtures, do not directly cause serious problems. For example, their buildup may be so slow that they can effectively be ignored or the system may be periodically flushed to remove the buildup. In some situations, however, such solid buildups can seriously disrupt a process by either substantially reducing the flow rate or altering a precise mixture. In some applications, such as power plant piping, the buildup of ash, corrosion or combustible by-products may clog passages and create erosive local hot spots within a pipe. Such buildups require prompt attention and measurement to allow appropriate corrections to restore the necessary flow conditions.

In U.S. Pat. No. 4,506,541 Cunningham discloses an apparatus for measuring the bulk density and mass flow rate of pulverized coal entrained in air using a beta radiation source. A beta particle source such as strontium-90 is placed behind a window on one side of a pipe passing the pulverized coal. The window allows beta particles to enter the interior piping channel. A detector located directly opposite the source and disposed within a windowed steel case monitors the number of beta particles which pass through the fluid duct into the detection chamber. Comparing the number of beta particles received by the detector to the number emitted by the source, facilitates the calculation of the bulk density and thus the mass flow of the powdered coal. A radiation opaque shield is disposed between the source and the detector to prevent beta particles from passing directly therebetween. The claimed advantage of this feature is to force the system to detect only scattered events, thereby increasing the total volume sampled. Unfortunately, such an approach also decreases the intensity of the signal received by the detector thereby requiring a relatively larger radiation source which is disadvantageous. More importantly, the window blocks a large percentage of the beta particle radiation, thereby further increasing the required source size.

In U.S. Pat. No. 4,463,263, Padawer discloses a positron-annihilation radiographic method and apparatus for nondestructively monitoring a specimen for density variations. A positron annihilation source is disposed between a pair of gamma ray detectors adapted for sensing the photons generated by positron annihilation events. The specimen being monitored is placed between the source and one of the detectors. Since annihilating positrons most often emit a pair of photons traveling in substantially opposite directions, a comparison of the gamma rays sensed by opposing detectors facilitate predictions about density variations within the specimen. However, Padawer contemplates interrogating the specimen with gamma rays as opposed to positrons. Thus, the device measures the attenuation of gamma rays which is inappropriate for precisely measuring the bulk density of low density materials and fluid streams. Further it does not contemplate monitoring the mass flow rate of a fluid.

Therefore, it is an object of the present invention to provide a nondestructive mass flow detector that uses a low level radiation source to monitor fluid flow.

Another object of the invention is to provide a mass flow rate measuring device that utilizes positron radiometry techniques to measure the mass flow.

Another object of the invention is to provide a radiometric mass flow monitoring technique that is capable of measuring flow through a vessel using the vessel wall as a detector.

Another object of the invention is to provide a bulk density measuring device that utilizes positron radiometry techniques to measure the bulk density.

To achieve the foregoing and other objects in accordance with the present invention, a device for measuring bulk density of material and/or mass flow of a material stream through a vessel is disclosed. The mass flow detector includes a positron source and an annihilation region disposed such that some of the positrons generated by the source must pass through the interior of the vessel before reaching the annihilation region. A gamma ray detector preferably located externally to the vessel detects the absorption of positrons within the annihilation region. Preferably, the annihilation region forms part of the vessel wall.

In a method aspect of the invention, either the bulk density or the mass flow rate of a material is measured by directing a known number of positrons across the material being measured. The effects of the material has on the positrons is measured and predictions about bulk density and/or the mass flow rate are made based o such effects.

The features of the present invention that are believed to be novel are set forth with particularity in the appended claims. The invention, together with further objects and advantages thereof, may best be understood by reference to the following description taken in conjunction with the accompanying drawing in which:

FIG. 1 is a schematic view of a positron annihilation measurement configuration in accordance with the present invention.

FIG. 2 is a schematic view of a mass flow rate detector constructed in accordance with the present invention for monitoring flow rate through a pipe.

FIG. 3 is a schematic view of an alternative embodiment of a mass flow rate detector constructed in accordance with the present invention.

Positrons are emitted during the beta decay of several neutron-poor nuclides. A good example of a positron emitting isotope is cobalt-56 which decays with a 77.7 day half-life to iron-56 by emitting a positron and several different gamma rays. The positrons are emitted with a distribution of energy less than about 1.5 MeV. Thus, positrons are quickly slowed down and absorbed in dense matter. In fact, the most energetic positrons emitted by Co-56 will only travel about 18 feet in air. When the positrons are absorbed, they combine and mutually annihilate with electrons and most often produce exactly two photons each having an energy level of 0.511 MeV. The gamma rays which are produced from positron annihilation are characteristically much more penetrating than the positrons themselves and can easily be detected through the walls of typical vessels.

The positron detection device differs from most radiometric monitoring systems (such as gamma ray and beta particles systems) which detect either direct or scattered radiation in the same form as it is in when generated. In contrast, a positron detection device as described herein attempts to measure the absorption of positrons which characteristically are associated with the generation of a pair of gamma rays. Thus, while positrons are very sensitive to changes in the media through which they flow, the photons which are generated from an annihilation event have good penetrating properties and may be readily detected through relatively thick walls.

The basic construction of a positron detection device will be described with reference to FIG. 1. The positron source 3 is placed on one side of an attenuator 5 having a gap 7. The attenuator 5 is formed of a material that is opaque to positrons. A positron absorber that includes an annihilation region 9 is positioned on the opposite side of attenuator 5 such that positrons passing through gap 7 will fall upon and be absorbed by the positron absorber within the annihilation region 9. The positron absorber may be made of a material with a low atomic number to reduce back scatter and optimize absorption. However, materials such as steel will also be effective. As discussed above, the absorption of a positron will typically produce a pair of photons having a specific energy level. A gamma ray detector 11 is positioned to detect the photons produced by the annihilation events. Thus, it will be appreciated that in order to precisely monitor the annihilation events, the gamma ray detector 11 must be collimated to exclude radiation from the source 3 since most positron sources also emit gamma rays.

Referring next to FIG. 2, a pipe monitoring configuration of the invention will be described. A vessel 15 is fitted with a positron source 3 which is disposed on one side of vessel 15 and is protected from abrasion. Such an installation is most easily accomplished by recessing the positron source 3 within a fitting or port 18. It will be appreciated that the positron source 3 could alternatively be embedded directly in the vessel wall as well. Provided that the positron source 3 is sealed, and since it may be extremely small, no windows or other screens are required to protect the positron source from the fluid stream. The low intensity of the positron source 3 eliminates any concerns about radiation hazards in the event of a fire in vessel 15. Compressed air may be channeled into port 18 through an air line 20 to keep the interior of port 18 free of debris.

The positron source 3 initially consists of a known quantity of a positron emitting element such as cobalt-56 or sodium-22. Radioactive decay of positron source 3 causes a predictable number of positrons to pass through the interior channel within vessel 15. Any material within vessel 15 will tend to slow and scatter the positrons, as well as absorb a few. The number of positrons absorbed by fluid passing through vessel 15 or precipitate formed on its walls will depend upon the bulk densities of those materials. Similarly, the amount of positron scattering will be correlated to the density of the materials within the vessel. Any of the positrons that are directed across the fluid stream and are not absorbed by the stream will be absorbed by the vessel walls. By monitoring the number of positrons absorbed by a specific segment of the vessel wall, referred to as annihilation region 17, the bulk density of the materials within the vessel can be accurately predicted.

It will be appreciated that a bulk density of 2.1 g/cm$^2$ any material will stop even the most energetic naturally occurring positrons (positrons of 4.15 MeV generated by Gallium 66). Therefore, any rigid pipe not made of foil will stop all naturally occurring positrons. If the vessel walls absorb less than all of the positrons passing therethrough, the bulk density calculations can be calibrated based on the opacity of annihilation region 17 to positrons. Similarly, if the vessel walls are extremely thin, an absorption plate (not shown) formed of a more substantial material could be placed behind the vessel walls to function as the annihilation region 17.

A gamma ray detector 11 is collimated by shield 19 to view a restricted annihilation region 17 within the walls of vessel 15. Shield 19 may be formed of any material that is opaque to gamma rays. By way of example, an appropriate shield material is lead. The shield 19 should collimate the gamma ray detector's view of the vessel 15. This is necessary not only to filter out photons generated by positrons absorbed within the vessel chamber, but also to shield the detector 11 from gamma rays generated by the positron source 3.

The gamma ray detector 11 may be placed such that it views any section of the vessel wall. Two alternative mounting techniques are shown in FIGS. 2 and 3. FIG. 2 contemplates mounting the gamma ray detector such that it views a particular section of the vessel wall such as the region of vessel 15 located directly across from positron source 3. Such a mounting structure is well suited to detect positrons that pass substantially through the vessel 15.

FIG. 3 shows an alternative positioning of the gamma ray detector 11. In this embodiment, gamma ray detector 11 is positioned directly opposite positron source 3 and a shield 21 is positioned between the two in order to prevent gamma rays from passing directly from positron source 3 to gamma ray detector 11. Shield 21 is sized such that gamma ray detector 11 views the walls of vessel 15 on each side. Such a layout is particularly useful for systems in which substantial scattering is expected.

It will be appreciated that the gamma ray detector 11 may actually view a portion of the interior of the vessel 15. With such an arrangement, positrons annihilated within the viewed portion of the vessel are detected as well as positrons annihilated within the annihilation region 17. In some circumstances this may be desirable to monitor scale buildup. In others it is not particularly problematic since the bulk density and mass flow calculations can be calibrated to account for such effects.

As will be appreciated by those skilled in the art, the bulk density of the materials within the vessel can be readily calculated using conventional techniques given the data provided by a device built in accordance with the present invention. Specifically, a calibration test is performed to experimentally determine the effects of a fluid stream on the positron flow over a wide variety of flow conditions. By way of example, a suitable positron source for monitoring the flow of a pulverized coal/air mixture through a 14-inch diameter steel pipe would be about 10 microcuries of cobalt-56.

It will be appreciated that the present invention may also be utilized to detect the buildup of precipitates on the walls of the vessel. Specifically, the effects that a precipitate will have on the positron beams can be experimentally determined. The existence of precipitates may then be either directly or indirectly measured. Direct measurements are possible since the precipitates themselves may cause unnatural scattering or increased absorption within the vessel. The existence of precipitates in places outside of the monitored area can be detected indirectly by observing decreases in the systems mass flow rate. In either event, experimentally derived profiles may be saved for comparison with profiles generated during actual use to facilitate prediction of scale and precipitates within the vessel.

Although the present invention has been described particularly as it relates to a specific embodiment, it should be understood that the present invention may be embodied in many other specific forms without departing from the spirit or scope of the invention. Particularly, it should be understood that the bulk density measuring device could be adapted to measure the bulk density characteristics of a wide variety of flowing as well as static materials. For example, the wetness of steam within a vessel such as either a steam turbine or a pipe could be measured. To accomplish the former, by way of example, the positron source could be disposed within the steam turbine itself. For applications such as the latter, where uniformity in material density as expected, a self contained unit could be constructed having a positron source mounted thereon and an absorption plate spaced apart from the positron source. Additionally, there are a number of well known positron emitting sources other than cobalt-56 and sodium-22 which may be suitable for particular applications.

While it is preferred that the annihilation detector region be formed from the vessel wall, the invention is not so limited. Thus, an annihilation plate could be disposed within a fluid stream or to a vessel wall that is sufficiently thin that it does not stop a sufficient number of positrons. Further, it will be appreciated by those skilled in the art that the actual positioning of the positron source and gamma ray detector could be widely varied as well. Thin windows formed of materials that are sufficiently thin to appear substantially transparent to positron flow could be used to shield the positron source from a corrosive environment when necessary. Similarly, it will be appreciated that the actual positioning of the gamma detector may be widely varied within the scope of the present invention. Therefore, the present examples are to be considered illustrative and not restrictive, and the invention is not to be limited to the details given herein, but may be modified within the scope of the appended claims.

We claim:

1. A device for measuring the mass flow rate of a material through a vessel having walls, the device comprising:

a positron source for emitting positrons;

an annihilation region spaced apart from the positron source for absorbing positrons generated by the positron source, then annihilation region forming a portion of the vessel walls and being positioned such that at least a portion of the measured material must pass between the positron source and the annihilation region; and a gamma ray detector externally of the vessel and shielded from the positron source for detecting gamma rays generated by the absorption of positrons within the annihilation region.

2. A device for measuring bulk density of materials within a vessel having walls comprising:

a positron source;

an annihilation region spaced apart from the positron source for absorbing positrons generated by the positron source, the annihilation region being positioned such that at least a portion of the measured material must pass between the positron source and the annihilation region; and a gamma ray detector disposed externally of the vessel and shielded from the positron source for detecting gamma rays generated by the absorption of positrons within the annihilation region.

3. A device for measuring bulk density as recited in claim 2 further comprising a housing for receiving the positron source.

4. A device for measuring bulk density as recited in claim 3 wherein said housing includes a window that is substantially transparent to positrons.

5. A device as recited in claim 2 wherein information provided by the gamma ray detector is used to estimate the mass flow rate of a material stream through the vessel.

6. A device as recited in claim 5 wherein the material stream includes powdered coal.

7. A device for measuring bulk density as recited in claim 2 further comprising a lead shield that collimates said gamma ray detector from said positron source.

8. A device for measuring the bulk density of materials within a vessel having walls, the device comprising:
   a positron source for emitting positrons;
   an annihilation region spaced apart from the positron source for absorbing positrons generated by the positron source, the annihilation region being positioned such that at least a portion of the measured material must pass between the positron source and the annihilation region, the annihilation region forming part of the vessel wall; and
   a gamma ray detector shielded from the positron source for detecting gamma rays generated by the absorption of positrons within the annihilation region.

9. A device for measuring bulk density as recited in claim 8 wherein said positron source is disposed within the vessel walls.

10. A device for measuring bulk density as recited in claim 8 wherein said gamma ray detector is located externally of the vessel.

11. A device for measuring bulk density as recited in claim 10 wherein the positron source is cobalt-56.

12. A device for measuring bulk density as recited in claim 10 wherein the positron source is sodium-22.

13. A device for measuring bulk density as recited in claim 10 wherein said annihilation region is formed of a portion of the vessel wall located opposite the positron source.

14. A device for measuring bulk density as recited in claim 10 wherein said gamma ray detector is collimated to prevent viewing the region of the vessel wall located opposite of the positron source.

15. A device for measuring the bulk density of materials within a vessel having walls, the device comprising:
   a positron source for emitting positrons;
   an annihilation region spaced apart from the positron source for absorbing positrons generated by the positron source, the annihilation region being positioned such that at least a portion of the measured material must pass between the positron source and the annihilation region; and
   a gamma ray detector shielded from the positron source for detecting gamma rays generated by the absorption of positrons within the annihilation region, wherein information provided by the gamma ray detector is used to estimate the wetness of steam within the vessel.

16. A device as recited in claim 15 wherein the vessel is a steam turbine and the positron source is disposed within the turbine.

17. A method of measuring mass flow of a fluid comprising the steps of:
   causing a positron source to direct positrons across the mass flow to be measured;
   detecting the effect of the mass flow on the positrons directed across the mass flow; and
   estimating the mass flow rate based upon the detected effects o the positrons.

18. A method of measuring the mass flow rate of a stream through a vessel having walls, the method comprising the steps of:
   directing a predictable supply of positrons across a selected portion of the vessel;
   measuring the number of positrons that successfully pass through the selected vessel portion by detecting gamma rays emitted by the absorption of positrons within an annihilation region that forms a portion of the vessel wall; and
   estimating the mass flow rate based upon the measured number of positrons that pass through the selected vessel portion.

19. A method of measuring the bulk density of material flowing through a vessel, the method comprising the steps of:
   directing a predictable supply of positrons across a selected portion of the vessel;
   measuring the number of positrons that successfully pass through the selected vessel portion using a detector located externally of the vessel, wherein the detector is shielded from the positron source and measures gamma rays emitted by the annihilation of positrons within an observed annihilation region within the vessel;
   estimating the bulk density of the material flowing through the vessel based upon the detected number of positrons that pass through the selected vessel portion.

20. A device for measuring the bulk density of a material the device comprising:
   a positron source;
   a positron absorber having an annihilation region spaced apart from the positron source for absorbing positrons generated by said source, the annihilation region being positioned such that the measured material is disposed between the positron source and the annihilation region;
   a housing that carries the positron source and the annihilation region; and
   a gamma ray detector that is shielded from the positron source for detecting gamma rays generated by the absorption of positrons within the annihilation region.

* * * * *